United States Patent [19]
Heath

[11] Patent Number: 6,109,537
[45] Date of Patent: Aug. 29, 2000

[54] RELEASE RATE MODULATOR AND METHOD FOR PRODUCING AND USING SAME

[75] Inventor: Robert R. Heath, Gainesville, Fla.

[73] Assignee: The United States of America as represented by the Secretary of Agriculture, Washington, D.C.

[21] Appl. No.: 09/252,945

[22] Filed: Feb. 18, 1999

[51] Int. Cl.$^7$ .................................................. A61L 9/04
[52] U.S. Cl. ............................... 239/6; 239/51.5; 239/55; 239/57; 239/58
[58] Field of Search .............................. 239/51.5, 49, 44, 239/56, 55, 53, 59, 58, 57, 6, 34; 43/107, 129, 131, 132.1; 428/905

[56] References Cited

U.S. PATENT DOCUMENTS

| | | | |
|---|---|---|---|
| 2,766,066 | 10/1956 | Hopson et al. | 239/44 X |
| 3,951,622 | 4/1976 | Wilk | 55/16 |
| 3,961,628 | 6/1976 | Arnold | 128/260 |
| 4,160,335 | 7/1979 | Von Kohorn et al. | 43/131 |
| 4,356,969 | 11/1982 | Obermayer et al. | 239/6 |
| 4,614,299 | 9/1986 | Van Louvern et al. | 239/6 |
| 4,979,673 | 12/1990 | Wilk | 239/6 |

OTHER PUBLICATIONS

Murphy, R.E., Heath, R.R., and Dorsey, J.G., "The optimization of capacity and efficiency when coupling fused silica open tubular columns in gas chromatography," Chromatographia 37(½):65–72 (1993).

Heath, R.R., Landolt, P.J., Dueben, B., and Lenczewski, B., "Identification of floral compounds of night–blooming jessamine attractive to cabbage looper moths," Environ. EntomoL 21(4):854–859 (1992).

Heath, R. R., and A. Manukian. "Development and evaluation of systems to collect volatile semichemicals from insects and plants using a charcoal–infused medium for air purification," J. Chem. Ecol. 18(7):1209–1226 (1992).

Heath, R. R., D. L. Chambers, J. H. Tumlinson, and P. J. Landolt. "A controlled release formulation of trimedfure isomer C and its attractiveness to the Mediterranean fruit fly (Diptera: Tephritidae)," J. Econ. Entomol. 83(3):819–822 (1990).

McGovern, T.P., Cunningham, R.T.–, and Leonhardt, B.A., "Attraction of trans–trimedlure and its four isomers in field tests with the Mediterranean fruit fly (Diptera: Tephritidae)," J. Econ. Entomol. 80:617–620 (1987).

Chuman, T., Landolt, P.J., Heath, R.R., and Tumilson, J.H., "Isolation, identification, and synthesis of male–produced sex pjermone of papaya fruit fly, Joxotrypana curvicauda Gerstaecker (Diptera: Tephritidae)," J. Chem. EcoL 13(9)1979–1991 (1987).

McGovern, T.P., Cunningham, R.T., and Leonhardt, B.A., "cis–Trimedlure: attraction for the Mediterranean fruit fly (Diptera: Tephritidae) and isomeric structural assignments," J. Econ. EntomoL 79:98(1986).

Heath, R.R., Teal, P.E.A., Tumlison, J.H., and Mengelkoch, L.J., "Prediction of release ratios of multicomponent phermones from rubber septa," J. Chem. Ecol. 12(12):2133–2143 (1986).

(List continued on next page.)

*Primary Examiner*—Lesley D. Morris
*Attorney, Agent, or Firm*—M. Howard Silverstein; John D. Fado; G. Byron Stover

[57] ABSTRACT

A release rate modulator for use with membrane-based formulations systems to control the release of a substance. The release rate modulator is formed from perforated polypropylene containing approximately 36 holes/cm$^2$. Each hole is approximately 1 mm$^2$ in size. The flow of substance passes through the holes and the membrane before reaching the surrounding environment. The use of the modulator improves the duration of substance release and provides a more constant release of the substance compared to unpredictable release rates obtained when the formulations systems did not contain the modulator.

28 Claims, 14 Drawing Sheets

OTHER PUBLICATIONS

Leonhardt, B.A., McGovern, T.P., and Plimmer, JR., "Capillary GC analysis of trimedlure, the attractant for the 'Medfly'," J. High Resolut. Chromatogr. Commun. 5:430–431 (1982).

Kydonieus, A.F., Beroza, M., and Zweig, G. (eds.), "Insect suppression with controlled release pheromone systems," vol. 1 and 2., CRC Press, Inc., Boca Raton, FL (1982).

Leonhardt, B.A., and Beroza, M (eds.), "Insect pheromone technology: chemistryand applications,"American Chemical Society Symposium Series 190, American Chemical Society, Washington, D.C. (1982).

McGovern, T.P., Beroxa, M., Ohinata, K., Miyashita, D., and Steiner, L.F., "Volatility and attractiveness to the Mediterranean fruit fly of trimedlure and its isomers, and a comparison of its volatility with that of seven other insect attractants," J. Econ. Entomol. 59:1450–1455 (1966).

Beroza, M., Green, N., Gertler, S.I., Steiner, L.F., and Miyashita, "Insect atrractants: New attractants for the Mediterranean fruit fly," J. Agric. Food Chem. 9:361–365 (1961).

Newell, W., "Progress report on the Key West (Florida) fruit fly eradication project," J. Econ. EtomoL 29:116–120 (1936).

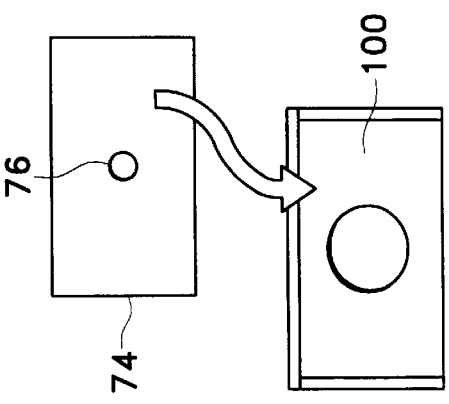
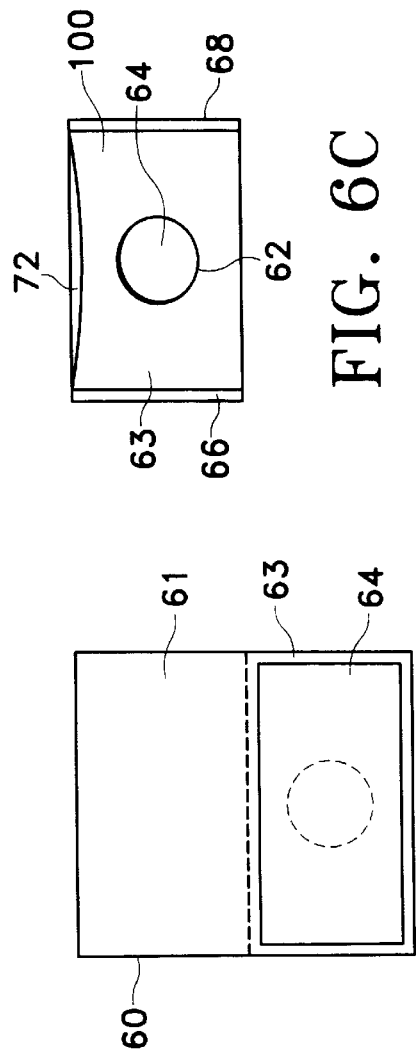
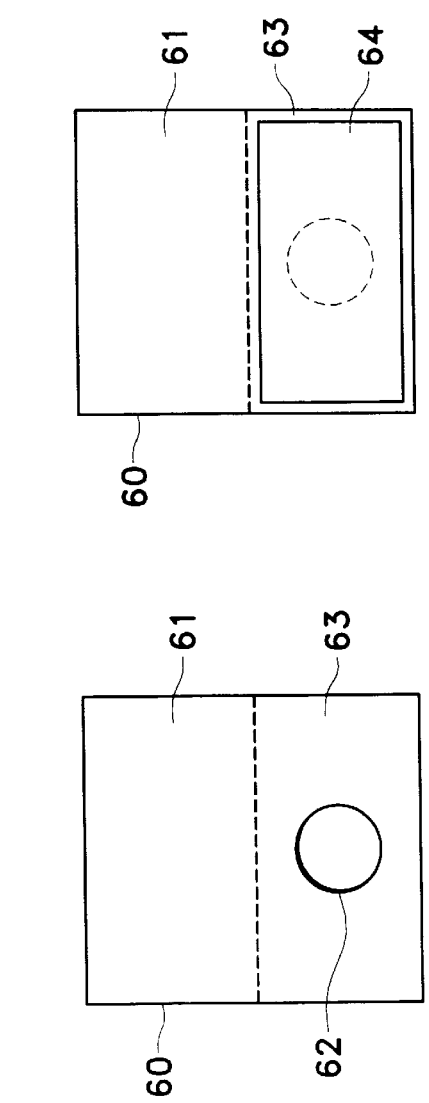
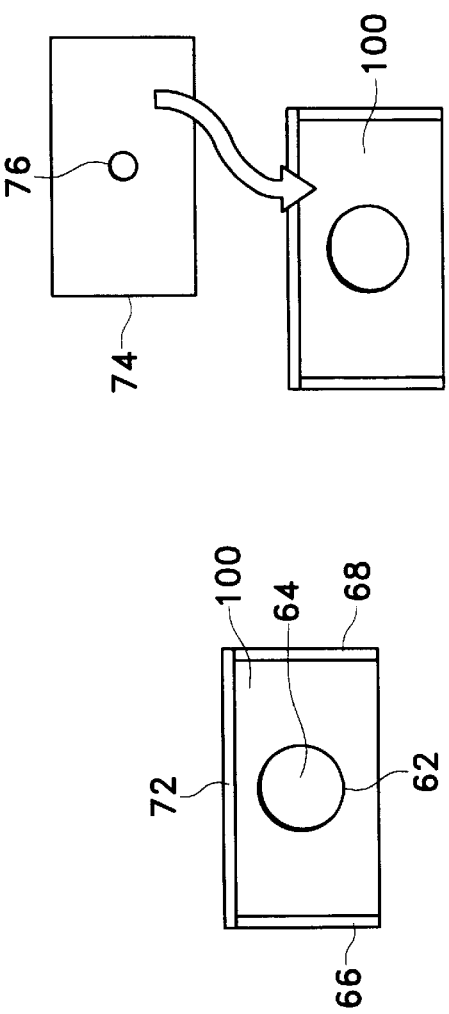
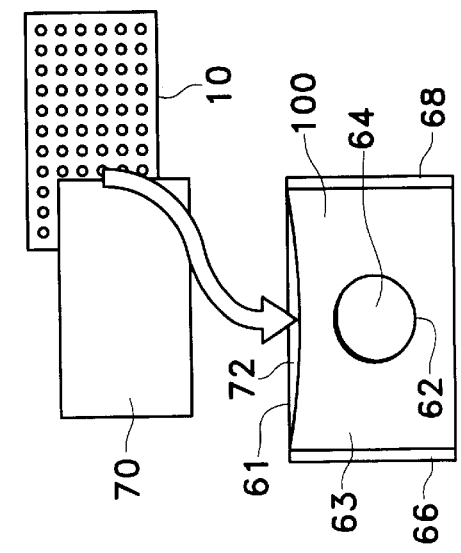

RELEASE RATE MODULATOR AND METHOD FOR PRODUCING AND USING SAME

BACKGROUND OF THE INVENTION

1. Field of the Invention

The present invention comprises an apparatus and method for the controlled release of a substance through a membrane-based formulation system. In particular, the invention relates to an apparatus and methods for controlling the rate of release of a substance through a membrane-based formulation system at substantially constant rates over long periods of time.

2. Background Art

Formulation systems for controlled release of chemical substance such as odors, fragrances, perfumes and insect semiochemicals are of considerable importance. They are widely used in agriculture, households, restaurants, hospitals and other daily life as well as commercial applications. For example, most chemical insect traps used in agriculture and daily life contain a lure. The lure is a formulation system for releasing a chemical substance to attract the targeted insects to the trap. Formulation systems designed for applications requiring large numbers of devices preferably should be economically constructed. The release of the chemical substance preferably should be persistent and consistent over an extended time period.

Considerable effort has been directed to the development of formulation systems for use in release of various chemical substances. More than 30 U.S. and foreign patents have been resulted. U.S. Pat. No. 4,614,299 issued to Van Louvern et al. summarized various apparatus and methods resulting from this effort and disclosed by inventors over the world, and itself disclosed a membrane-based formulation system which utilizes microporous polymers. Formulation systems are also described in numerous publications, reviews, book chapters and books. "Insect Suppression with Controlled Release Pheromone Systems" edited by Kydonieus, Beroza, and Zweig, CRC Press, Inc. Boca Raton, Fla. (1982), Vol. 1 and 2; and "Insect Pheromone Technology: Chemistry and Applications" edited by Leonhardt and Beroza, American Chemical Society Symposium Series 190, American Chemical Society, Washington, D.C. (1982) are examples of books addressing the subject.

Despite the fact that many compounds can be formulated with existing formulation systems there remains a need to increase the duration over which that the active substance is released, to provide a constant release rate over time, and to develop formulations with the ability to control the release of highly volatile chemicals. One particular problem associated with existing formulation systems such as rubber matrices, laminates, and polyvinyl polymers is that they do not provide constant release of highly volatile chemicals over the time periods needed for bioassays and field tests of many insect semiochemicals. As discussed in the paper "Prediction of Release Ratios of Multicomponent Pheromone from Rubber Septa", Heath, et al., J. Chem. Ecol., 12(12), 2133–2143 (1986), use of rubber septa as formulation devices is limited to compounds that have a vapor pressure of less than 1.0 Pa. Release rates of compounds with vapor pressures of approximately 1.0 Pa that have been loaded on rubber septa will typically decrease to one half of their original release rates (half-life) in approximately 14 days.

Methods to formulate highly volatile compounds using capillaries filled to variable heights have been described, for example, in the paper "Identification of Floral Compounds of Night-Blooming Jessamine Attractive to Cabbage Looper Moths", Heath, et al., Environ. Entomol., 21(4), 854–859 (1992). This formulation method provides systems for use in laboratory bioassays but is more difficult to use in the field because the capillary must be maintained in a vertical position and because the lure must be protected from adverse weather.

Membrane-based formulation systems, such as that disclosed in U.S. Pat. No. 4,614,299 issued to Van Louvern et al., have also been developed over the years. Of the different formulation systems available, membrane-based formulation systems appear to be the most cost effective. Because membrane-based formulation systems follow zero-order kinetics, they provide a constant emission of substance over time with a linear decrease in the amount of material remaining in the formulation. These systems use various materials such as particulates or pulverized fillers such as clay, limestone, silicates, polymers, etc., and/or extending agents such as high molecular weight polymers and various nonvolatile chemicals added to the active compound tested time periods. Currently, the commercially available formulation of trimedlure ("TML") that is most widely used is based on incorporation of 2 ml of trimedlure in a thermoset plastic plug manufactured by Magnet lure, AgriSense, Fresno, Calif. As disclosed in the paper "A Controlled Release Formulation of Trimedlure Isomer C and Its Attractiveness to the Mediterranean Fruit Fly (Diptera: Tephritidae)", Heath, et al., J. Econ. Entomol., 83(3), 819–822 (1990), this formulation releases isomer C at approximately 200 $\mu$g/hr and has a half-life of approximately 21 days, which is an improvement over other more involved systems such as laminates. However, in the recent experience of the inventor and that of United States Department of Agriculture—Animal and Plant Health Inspection Service (USDA-APHIS) personnel the formation of crystals on the surface of the plugs have been observed. These crystals were identified as isomer C based on gas chromatographic data and mass spectroscopy. These crystals often dislodge from the surface of the plug and potentially provide an attractive source away from the trap.

Finding a better formulation system becomes more urgent because of the great threat posed by various fruit flies to the well-being of agriculture around the world. It is estimated that California, Texas and Florida alone deploy an excess of 5,000 lures in the field per year to detect pest fruit flies. These lures typically must be replaced every two weeks because no active substance is released thereafter. Approximately 20 countries also use formulations of trimedlure to monitor for the Mediterranean fruit fly. These efforts, however, have been thwarted or at least weakened by lack of a suitable formulation. The inventor's recent efforts testing various fruit fly attractants, including the four component blend of hexanol, ethyl hexanoate, ethyl octanoate, and cineole, previously identified as food attractants from chapote for the Mexican fruit fly, experienced the same problems. In previous tests using materials that were formulated using rubber septa or formulations developed by Scentry® were unable to demonstrate biological activity as disclosed in the paper "A Novel Attractant for Mexican Fruit Fly, *Anastrepha Ludens*, from Fermented Host Fruit," Robacker, et al., J. Chem. Ecol., 16, 2799–2815(1990). This, combined with the crystallization problem associated with the current membrane-based formulation system, has prompted further investigation of alternative substance release mechanism and systems.

SUMMARY OF THE INVENTION

The present invention overcomes the disadvantages of the prior art and discloses a new approach to the development of formulation systems for use in the release of substances. Specifically, a mechanical release rate modulator, which does not require the admixing of materials, is utilized to cooperate with the existing membrane-based formulations to control the release of substance.

The formulation system constructed according to one embodiment of the present invention has a receptacle. The receptacle is formed from a material essentially nonpermeable to a substance to be released. The receptacle has an interior for containing the substance and at least one first opening to allow communication between the interior of the receptacle and the surrounding environment. A membrane selectively permeable to the substance is also contained within the receptacle. A release rate modulator of the present invention is positioned between the membrane and the substance to affect the release of the substance. The receptacle may be an envelope, a bag, a box, a container or other similar structure, or can be a reservoir for containing the substance in cooperation with an existing structure.

The modulator, in one preferred embodiment, is a perforated plate with a plurality of holes. Unlike the microporous character of the existing membrane-based formulation system, the holes of the present modulator are visible and macroscopic. The substance is modulated by the modulator so that it is not totally free to reach the membrane. Instead, the substance communicates with the membrane through the channels provided by the holes. The holes are large enough to allow a sufficient volume of the substance to reach the membrane but small enough to prolong the flow of substance. In other words, the modulator does not admix the substance but controls the flow rate of the substance reaching the membrane; the membrane receives a modulated incoming flow of the substance and then generates an outgoing flow of the substance in response. As a result, a relatively consistent flow of the substance is produced.

The present invention can be practiced to modulate the release of a wide range of substances. Any volatile material can be modulated by the device and method of the present invention. The volatile material may consist of insecticide compositions, herbicide compositions, perfume compositions, animal repellent compositions, air freshener compositions, pheromone compositions, odor maskant compositions, deodorant compositions, insect repellent compositions, compositions for the evaluation of olfactory functioning in humans as well as in animals and compositions for the treatment of disease of humans and animals through olfactory functioning.

A device for transfer of a substance to the surrounding environment according to another embodiment of the present invention has a receptacle containing the substance. The receptacle has at least one opening and a plate covering the substance. The plate has a plurality of holes providing channels for the substance to pass into the surrounding environment through the opening in a relatively consistent flow.

According to still another embodiment, the present invention comprises a device for releasing a substance to the surrounding environment having a backing for supporting the substance and a perforated plate with a plurality of holes covering the substance against the backing. In use, the plurality of holes allow the substance to communicate with the surrounding environment.

The use of the modulator improves the duration of chemical release and provides a relatively constant release of the compounds compared to unpredictable release rates obtained when the formulations did not contain the modulator. The utility of the modulator was determined in preparation of formulations that released varying amounts and ratios of the four chemicals. In addition to the four component Mexican fruit fly attractant the use of a membrane based formulation system with the modulator was evaluated for the formulation of several insect semiochemicals. These included 2-methyl-6-vinyl pyrazine previously identified as the male produced pheromone of the papaya fruit fly, and tert-butyl 4 (and 5) chloro-2-methylcyclohexane-I-carboxylate, aniale parapheromone used in detection of Mediterranean fruit flies. The results were surprisingly positive and encouraging. During the course of our investigations of trimedlure in the membrane-based formulation system containing the modulator, we did not observe crystals on the surface of these lures. More importantly, the average release rate over time is relatively constant over a prolonged period. According to one preferred embodiment used to control the release rate of isomer C, the average release rate is approximately 100 $\mu$g/hr more than that released by the existing commercial formulations and has a half-life of approximately 25 days. In light of these results it is believed that the present invention would reduce lure replacements by approximately 70% at the current nationwide consumption level.

One feature of the modulator according to the present invention is its compatibility with the existing membrane based formulation system. Any existing membrane based formulation system can be used to practice the present invention by simply placing the modulator next to the membrane.

Another aspect of the modulator of the present invention is that the modulator itself is easy to construct. According to one preferred embodiment, the modulator consists of a 1.0 mm thick piece of perforated polypropylene containing about 36 holes/$cm^2$. Each hole is approximately 1 $mm^2$ cross-sectionally. The modulator takes the shape of the lure container, normally rectangular or circular. The holes are distributed over the piece in an array, or a grid. For commercial use, the modulator of the present invention can be manufactured in great quantity in automation. An individual user, on the other hand, can simply install a panel of polypropylene or similar material providing a number of holes to modify an existing membrane-based formulation system or lure into a system according to the present invention. Therefore, practicing the present invention is economic and efficient.

The present invention accordingly aims to achieve at least one or combinations of the following objectives:

To provide a new apparatus and methods for controlled release of substance.

To provide a new apparatus and methods for controlled release of substance at a relatively constant rate over a prolonged time period.

To provide a new apparatus and methods for controlled release of substance at a relatively constant rate over a prolonged time period that uses a modulator to cooperate with a membrane based formulation, wherein the modulator is a perforated plate with a plurality of holes allowing the substance to communicate with the membrane.

To provide a new apparatus and methods for controlled release of substance at a relatively constant rate over a prolonged time period that uses a modulator to cooperate with a membrane based formulation, wherein the modulator is a perforated plate with a plurality of holes allowing the substance to communicate with the membrane and the holes are distributed over the plate substantially in a pattern.

To provide a new apparatus and methods for controlled release of substance at a relatively constant rate over a prolonged time period that uses a modulator to cooperate with an existing membrane based formulation, wherein the modulator is a perforated plate made from material nonpermeable to the substance.

To provide a modulator which can be used with a membrane based formulation system to form a device to control the release of substance, where the device can be easily made at a reduced cost with minimum labor.

To provide a new method for releasing substance that placing a perforated plate with a plurality of holes next to a membrane, wherein the plate modulates the flow of the substance by only allowing the substance to communicate with the membrane through the holes so that a relatively consistent flow of the substance is produced.

Other objects, advantages and uses for the present invention will be more clearly understood by reference to the remainder of this document.

BRIEF DESCRIPTION OF THE DRAWINGS

FIGS. 6(A)–(F) schematically shows steps for construction of a membrane-based formulation system or lure with a modulator according to one embodiment of the present inventions.

(Left y-axis legends are for cineole and ethyl octanoate and right y-axis legends are for hexanol and ethyl hexanoate.)

Figure 13:
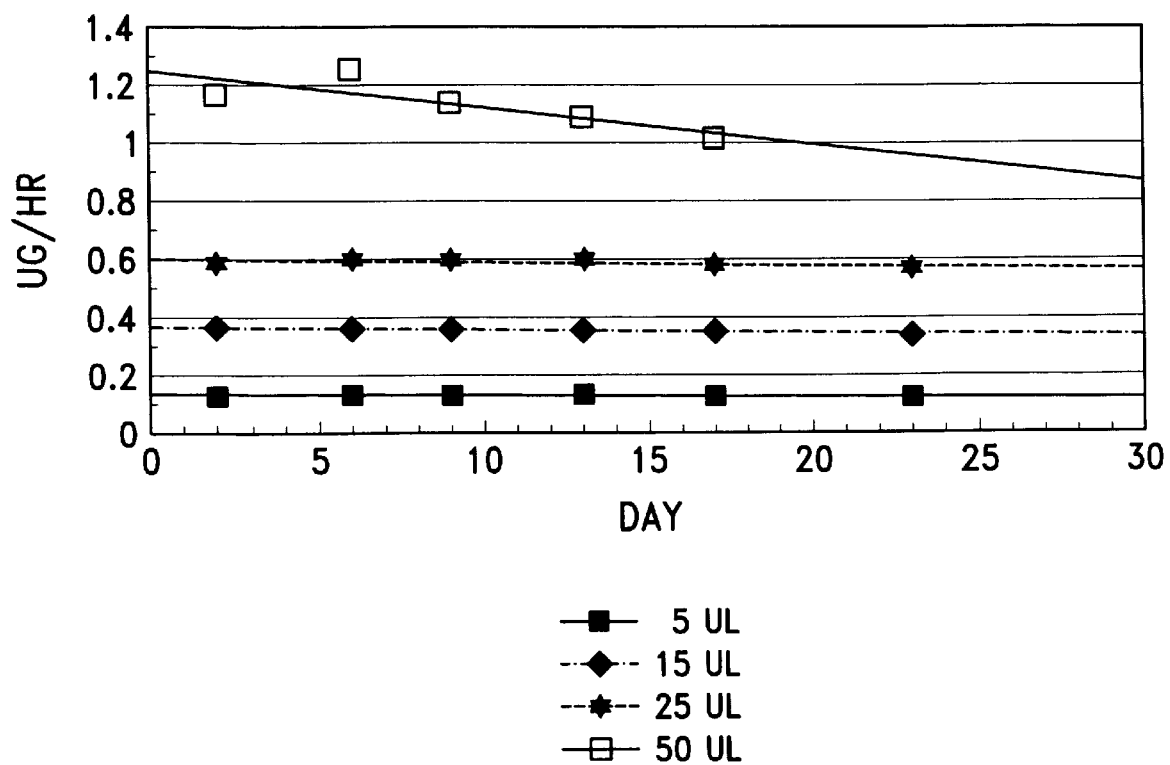

FIG. 13 charts the observed release rates from type 1 formulation with the modulator according to one embodiment of the present invention loaded with 5, 15, 25 and 50 $\mu$l of 2-methyl-6-vinyl pyrazine.

Figure 14A:
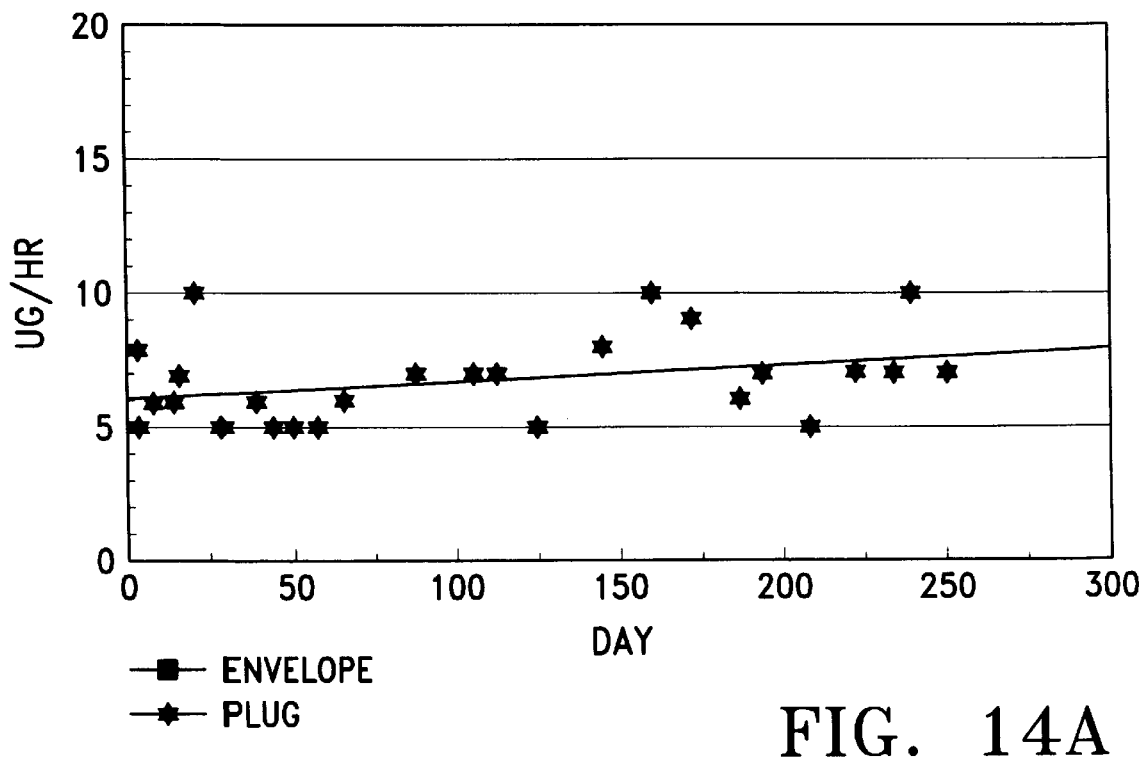
Figure 14B:
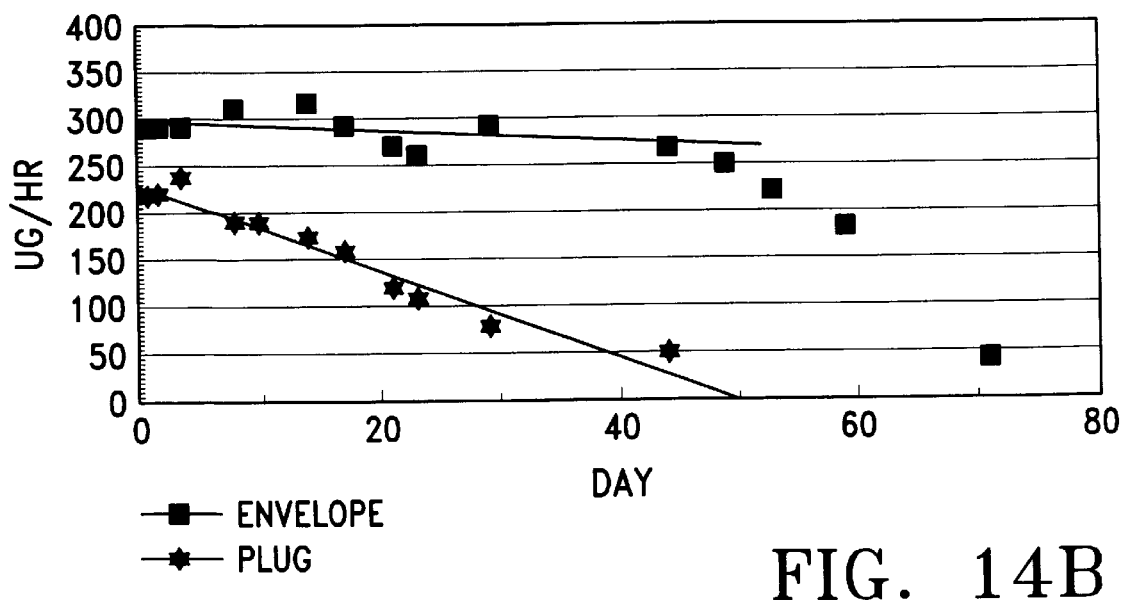

FIGS. 14(A)–(B) chart the observed release rates of TML from type 2 low density polyethylene lure, with the modulator according to one embodiment of the present invention but with different sized portions of the membrane exposed: (A) with a 1.17 cm diameter circle of membrane exposed; (B) with a 54 cm circle of membrane exposed (envelope) or from a commercial lure (plug).

DETAILED DESCRIPTION OF THE INVENTION

The present invention is more particularly described in the following examples that are intended as illustrative only since numerous modifications and variations therein will be apparent to those skilled in the art. As used in the specification and in the claims, "a" can mean one or more, depending upon the context in which it is used. The preferred embodiment is now described with reference to the FIGS. 1–14, in which like numbers indicate like parts throughout the FIGS. 1–14.

OVERVIEW

Referring generally to FIGS. 1–14, the present invention comprises a modulator that offers a facile and inexpensive formulation device and method when used in lures that employ different types of membranes. Based on the release rate data obtained using the modulator, the present invention provides a substantially constant emission of individual semiochemical components and blends of semiochemicals. No admixing is required and the release rate can be adjusted by lure load and exposed area of the membrane. The modulator of the present invention may facilitate field testing of attractants and provide a device and new mechanism to enhance research related to improved systems to attract, monitor and suppress pest insect populations among its many potential applications.

Figure 1:
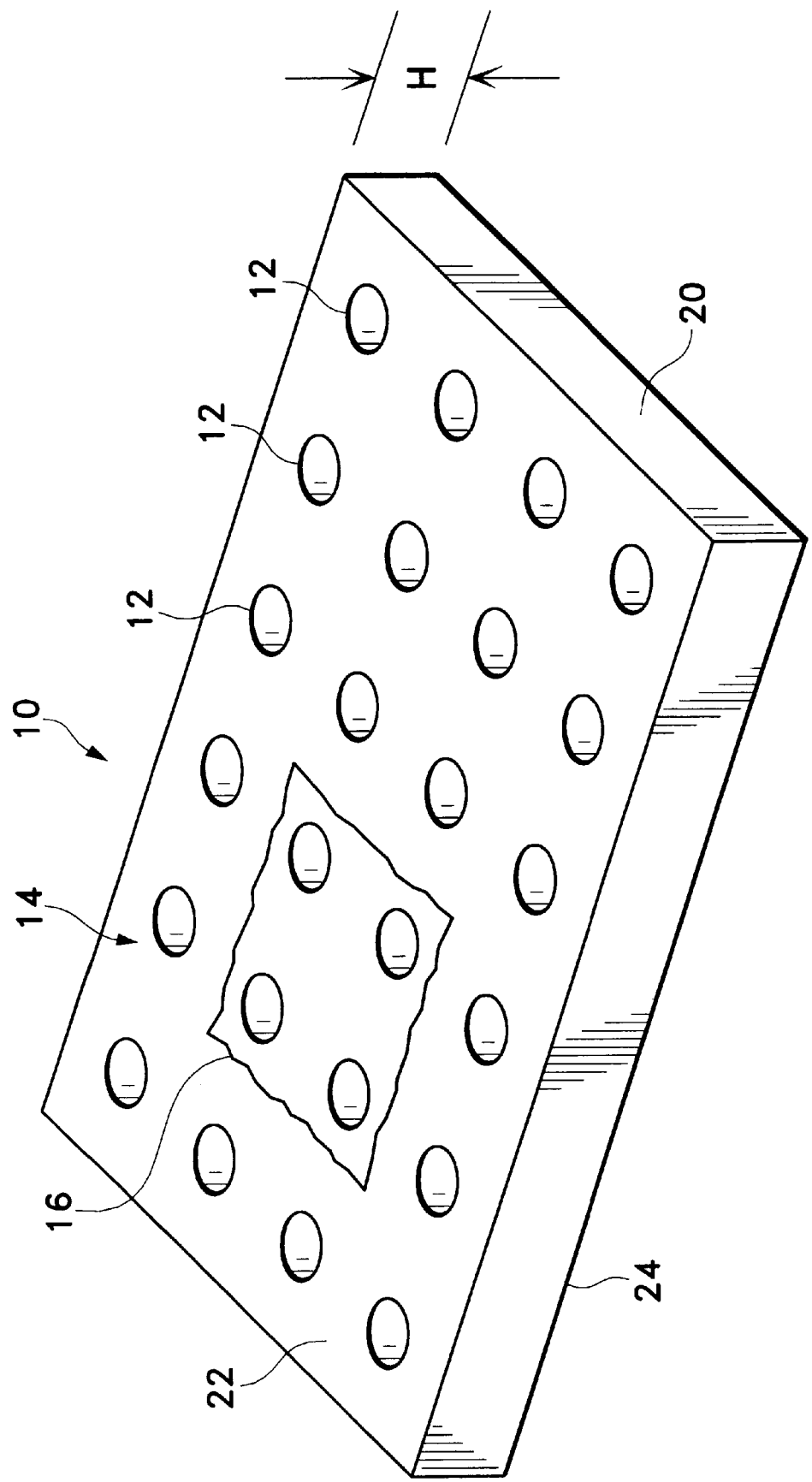
FIG. 1 is a perspective view of a release rate modulator according to a preferred form of the present invention.

Referring to FIG. 1, the modulator 10 of the present invention, according to one preferred embodiment, has a perforated plate 20 and a plurality of holes 12. The plate 20 has a first surface 22 and a second surface 24 opposing the first surface 22. The first surface 22 and the second surface 24 are substantially identical in size. The first surface 22 and the second surface 24 define a thickness H. The holes 12 are preferably distributed over the perforated plate 20 in a pattern. As shown in FIG. 1, that pattern is an array or grid 14 in this embodiment. Each element 16 of the array 14 is a square with four holes 12 at the four corners of the element 16. A density can be defined by the ratio of the total number of holes over the total area of the first surface 22.

Figure 2:
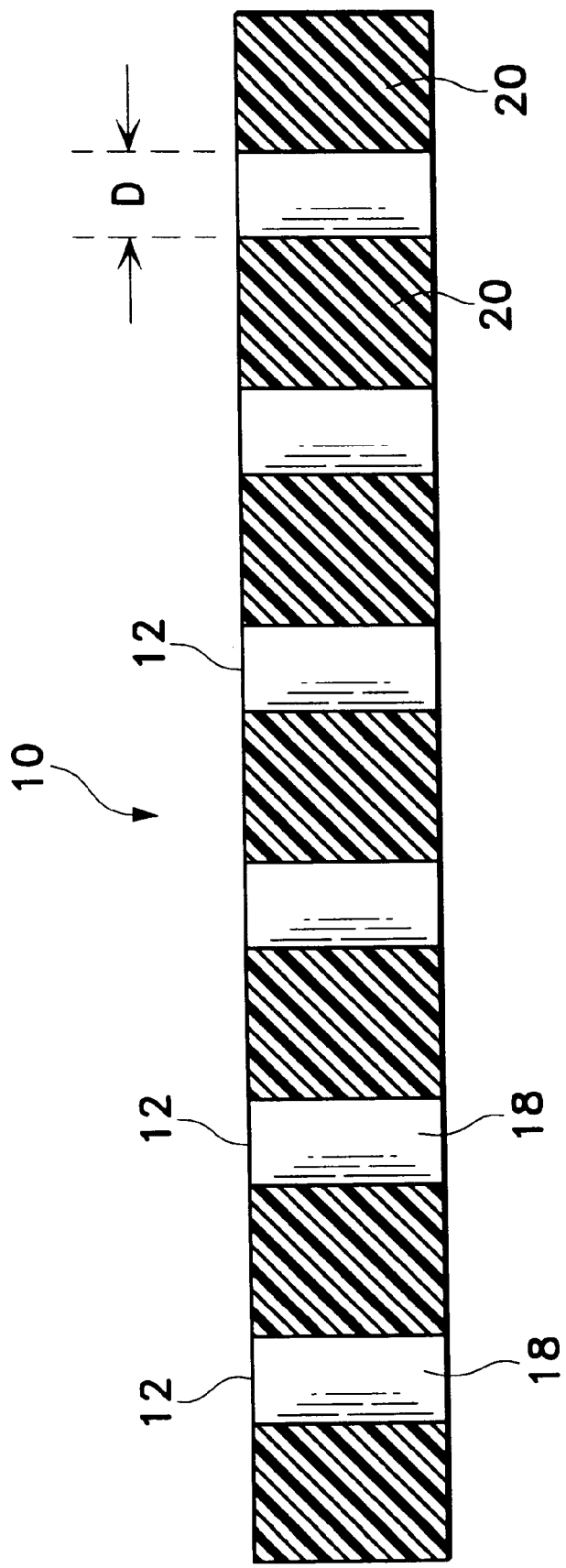
FIG. 2 is a cross-sectional view of the modulator in FIG. 1.

Each hole 12 has an interior 18 defining a channel extending from the first surface 21 to the second surface 24, or likewise. Cross-sectionally each hole may be circular, square, rectangular, triangular, diamond, oval or other geometrical shape. Accordingly, holes can be cylinders, cubic, cone or other geometric shapes. Holes can be different in shape. Roughly speaking, however, the cross-sectional area S of hole 12 can be estimated as $S = 0.25 \times \pi \times (D)^2$, where D is the diameter of a cylindric hole 12 as shown in FIG. 2. For the embodiment shown in FIG. 2, where holes 12 are cylindric, S is about 1 mm$^2$. To practice the invention, S should be in the range of 0.5 to 1.5 mm$^2$. The density is in the range of approximately 30 to 42 holes/cm², and more preferably approximately 36 holes/cm² is chosen. The thickness H is in the range of 0.5 to 2.0 mm, about 1 mm.

Figure 3:
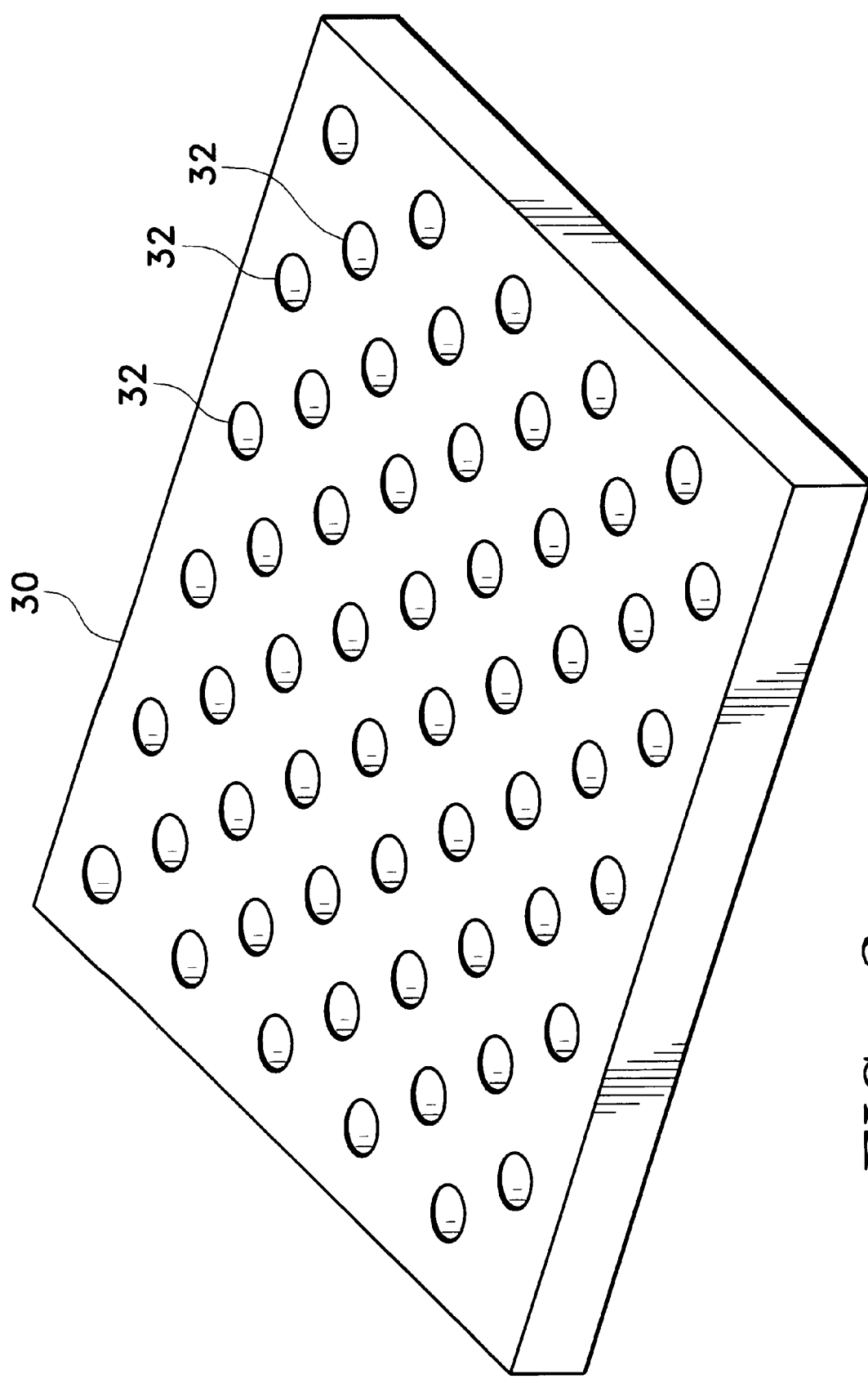
FIG. 3 is a perspective view of a first alternative embodiment of the modulator of the present invention.
Figure 4:
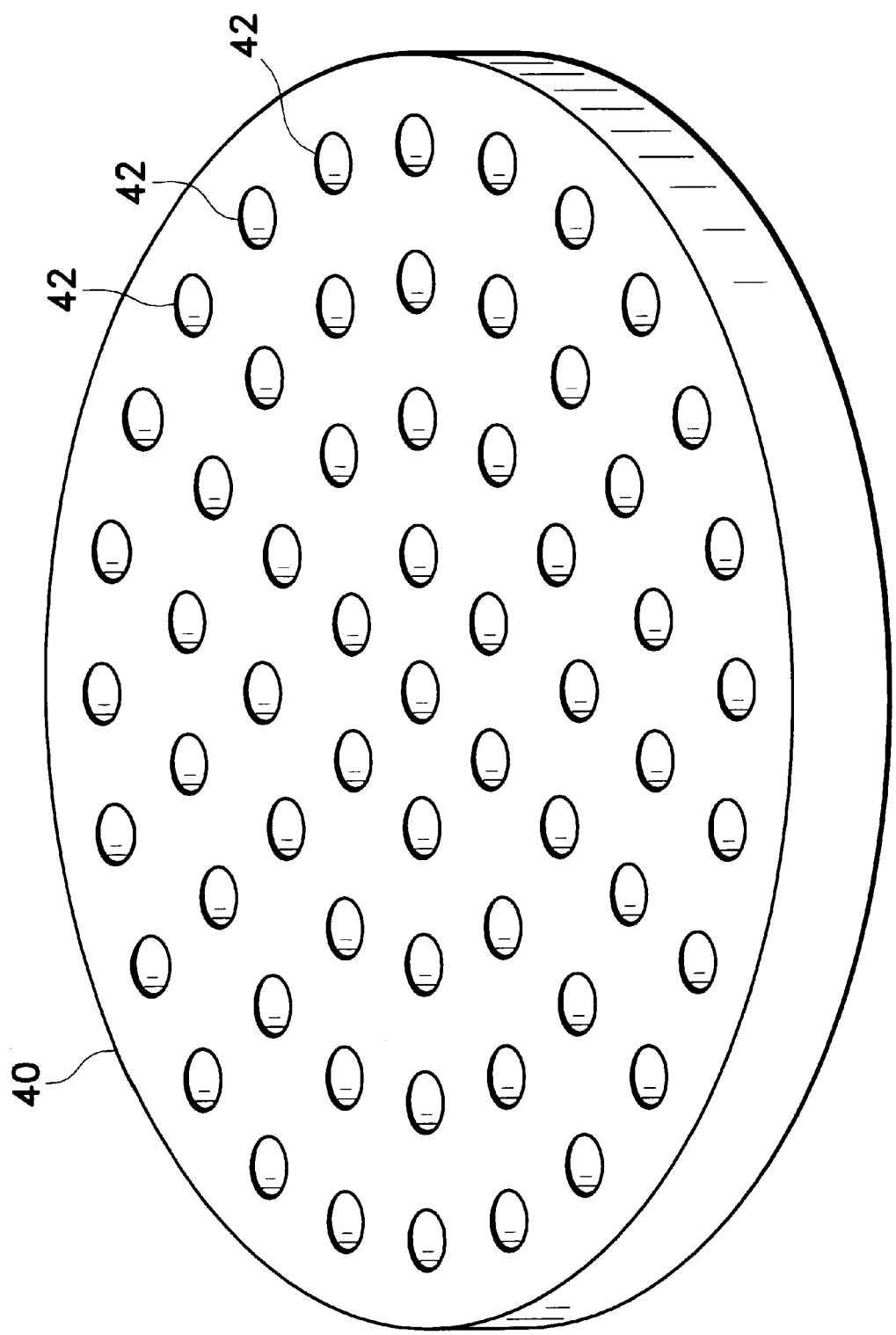
FIG. 4 is a perspective view of a second alternative embodiment of the modulator of the present invention.
Figure 5:
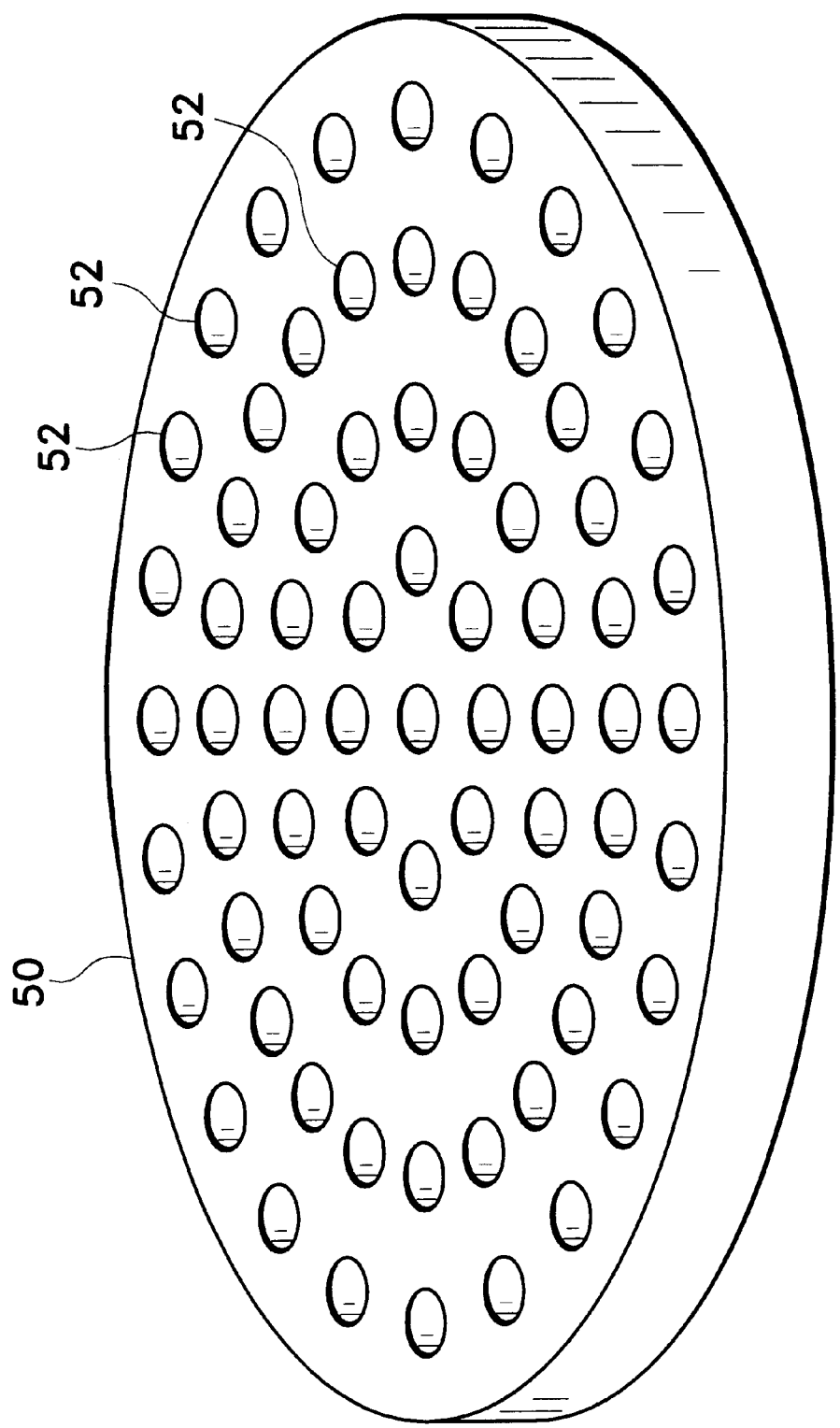
FIG. 5 is a perspective view of a third alternative embodiment of the modulator of the present invention.

Modulator 10 can take many alternative shapes with different arrangement of holes. FIG. 3 shows a first alternative embodiment of the modulator 10 shown in FIGS. 1 and 2. In FIG. 3, modulator 30 is generally square and has holes 32 arranged diagonally. FIG. 4 shows a second alternative modulator 40, which is circular. Modulator 40 has holes 42 arranged radially. FIG. 5 shows a third alternative modulator 50, which is oval. Modulator 50 also has holes 52 arranged radially. Many other alternatives are available, as people in the field will appreciate. For example, instead of being arranged in a pattern, holes 42 can be distributed over the plate randomly. By appropriate selection of the size, shape and hole arrangement, the modulator 10 can be integrated into many existing membrane-based formulation systems.

Modulator 10 can be made from polymer, plastic, metal, wood, artificial wood, paper or other similar material. Preferably, the material is nonpermeable to the substance. In the presently preferred embodiment, polypropylene is used because it is light weight, inexpensive, stable against adverse field conditions, and easy to punch with holes.

Once a modulator 10 is prepared, it can be used to construct a membrane-based formulation system or lure which is used to release a substance. Referring now to FIG. 6, a preferred method of construction is shown. As shown in FIG. 6(A), a nonpermeable backing 60 with a first opening 62 is provided. The backing 60 has a first portion 61 and a second portion 63, which are substantially identical in size and in shape. Alternatively, separate panels can be joined to form the first and second portions 61, 63. Opening 62 can be on either portion. For the embodiment shown in FIG. 6, it is on the second portion 63. For the embodiment shown, the opening 62 is located generally at the center of the second portion 63. Alternatively, the opening 62 can be located off the center, around the center, or at other positions. Moreover, more than one openings can be provided.

A membrane 64 is then placed on top of the second portion 63, as shown in FIG. 6(B). The membrane 64 can be rectangular as depicted, or of other space corresponding to and sized slightly smaller than the second portion 63 so that it can fit into the second portion 63. The membrane 64 is permeable to the substance.

As shown by FIG. 6(C), the first portion 61 of the backing 60 is folded against the second portion 63 to form an envelope 100 by sealing two open sides 66 and 68. The envelope 100 now has a side opening 72 in addition to the opening 62 on the second portion 63. The sides 66 and 68 can be sealed by heat sealing, sewing, gluing, taping, stapling or other kind of sealing used in the art. In the presently preferred embodiment, heat sealing is used.

The modulator 10 is placed into the envelope 100 through the side opening 72 as shown in FIG. 6(D). The modulator 10 is positioned between the first portion 61 and the membrane 64. In other words, the modulator 10 divides the interior of the modulator 10 into a first chamber and a second chamber. The first chamber contains the membrane 64. The second chamber is filled with chemical substance. Alternatively, the modulator 10 may be placed into the position before the envelope 100 is formed. An optional filter paper 70 may be placed into the second chamber. The chemical substance can be pipetted onto the filter paper 70 beforehand. The filter paper 70 with the chemical substance can then be placed into the envelope 100. As a further alternative, the filter paper 70 may be placed into the envelope 100 first and the chemical substance is then pipetted into the space between the modulator 10 and the filter paper 70.

The envelope 100 is completed by sealing the side opening 72. The side opening 72 can be sealed by heat sealing, sewing, gluing, taping, stapling or other kind of sealing used in the art. In this embodiment, it is sealed by heat sealing. At this stage, only the membrane 64 can directly communicate with surrounding environment through the opening 62. In other words the membrane 64 is exposed to the surrounding environment through the opening 62.

Optionally, as shown in FIG. 6(F), a film or tape 74 with an opening 76 can be placed over the second portion 63 of the envelope 100 to adjust the size of the opening 62. The tape 74 is nonpermeable to the substance and the size of the opening 76 may be same or different from that of the opening 62. Placing the tape 74 with the opening 76 over the opening 62 thus effectively reduces the area of the membrane 64 directly exposed to the surrounding environment. Furthermore, the tape 74 can be placed over the second portion of the envelope 100 in a movable fashion so that the overlap of the opening 76 and the opening 62 can be changed from zero to the full scope of the opening 62 or vice versa by sliding the tape 74 or the envelope 100.

Figure 7:
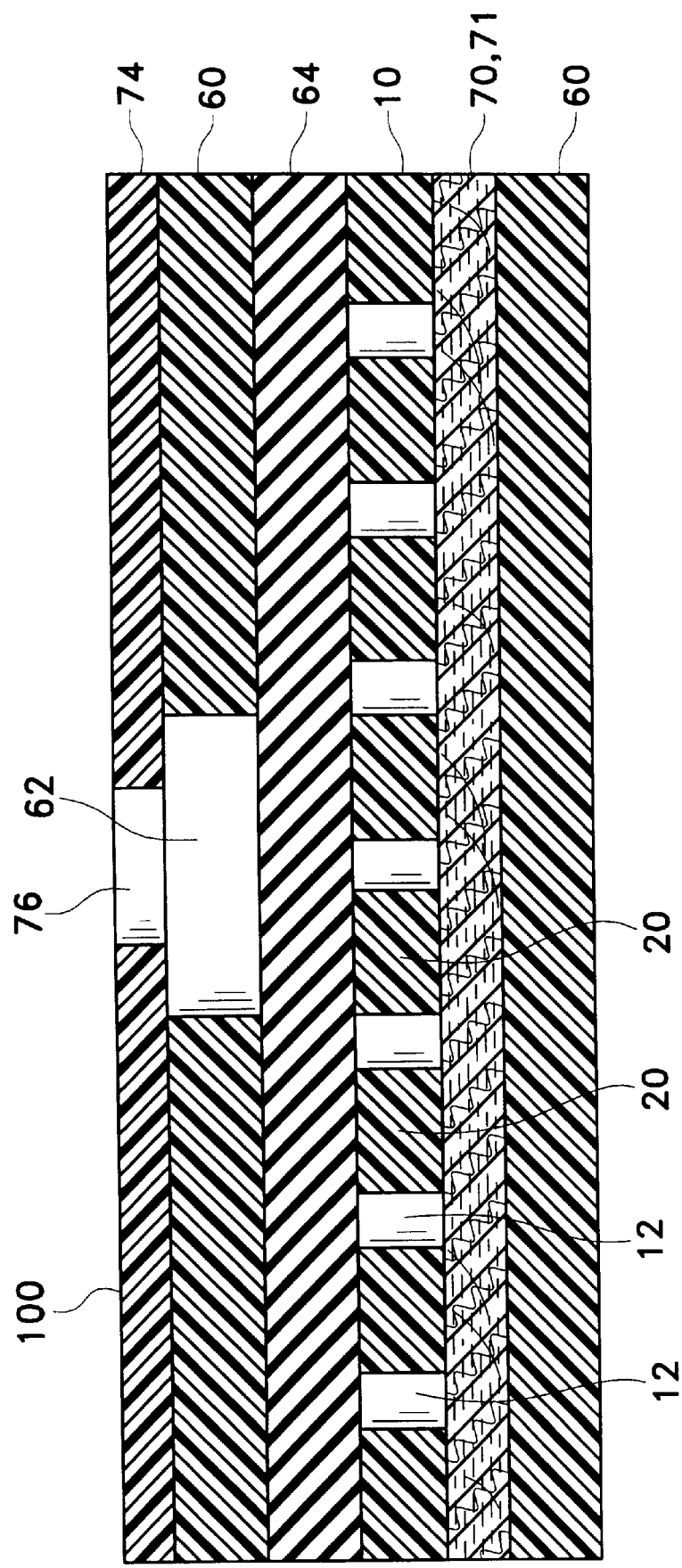
FIG. 7 is a cross-sectional view of the system shown in FIG. 6.

In sum, as shown in FIG. 7, the completed envelope 100 contains the filter paper 70 pipetted with the chemical substance, the modulator 10 with an array of holes 12, and the membrane 64 next to the modulator 10. The membrane 10 communicates with the surrounding environment through the opening 62, which is adjustable by appropriate positioning of the tape 74 with the opening 76. The substance 71 passes through the channels offered by the holes 12 of the modulator 10, reaching the membrane 64 in a modulated flow. The flow of the substance is further regulated by the membrane 64 so that a relatively consistent flow of the substance is released from the openings 62, 76. The envelope 100, thus constructed, is ready to be used as a membrane-based formulation system or lure.

The steps illustrated in FIGS. 6A (A)–(F) may be practiced in different orders. For example, the membrane 64 can be placed into the envelope 100 after the modulator 10 is in place. Some steps can also be combined. The modulator 10 and the membrane 64, for instance, can be placed next to each other first to form an "assembly" and then the assembly is put into the envelope 100.

Figure 8:
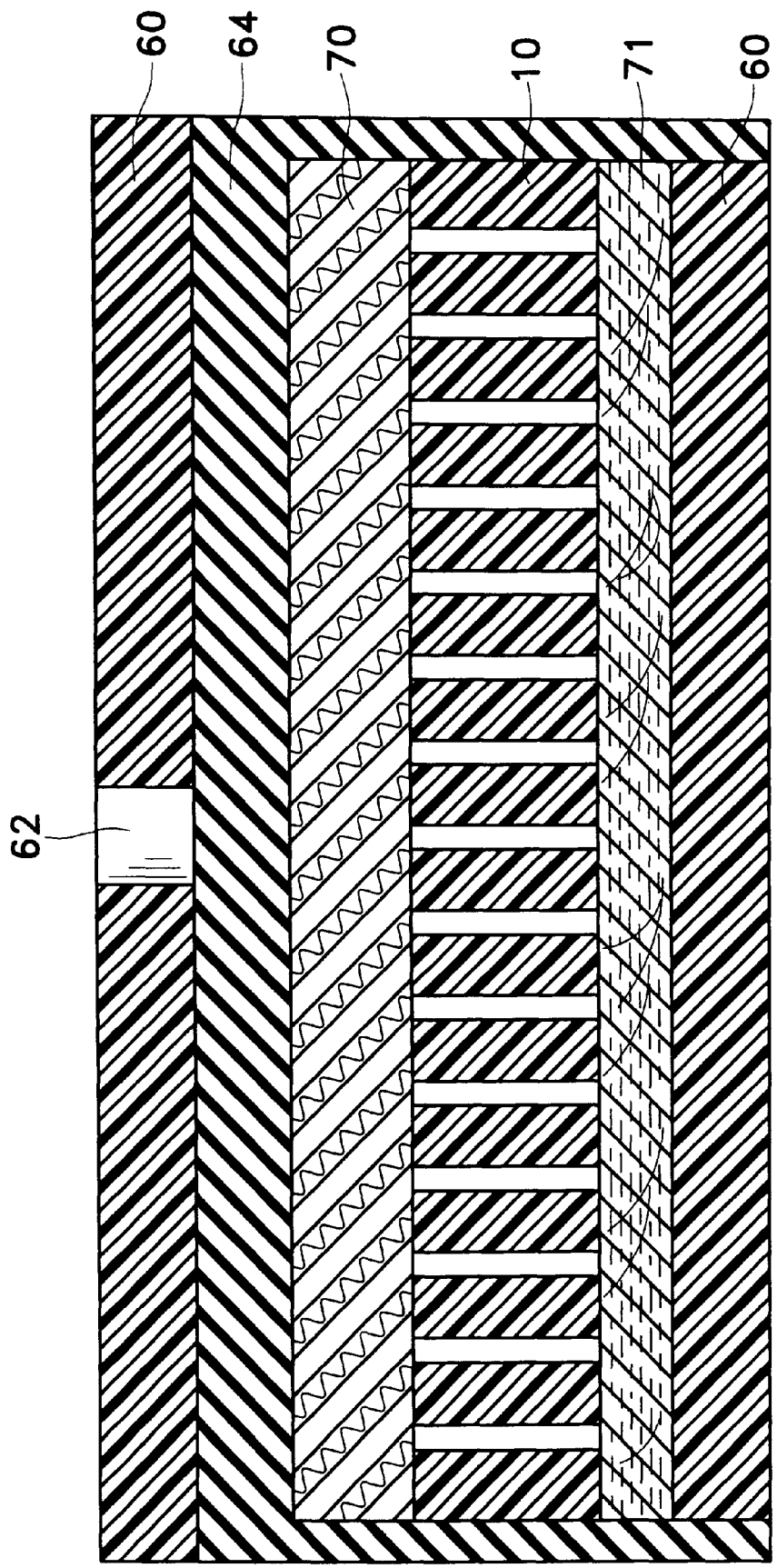
FIG. 8 is a cross-sectional view of a first alternative embodiment of the membrane-based formulation system of the present invention.
Figure 9:
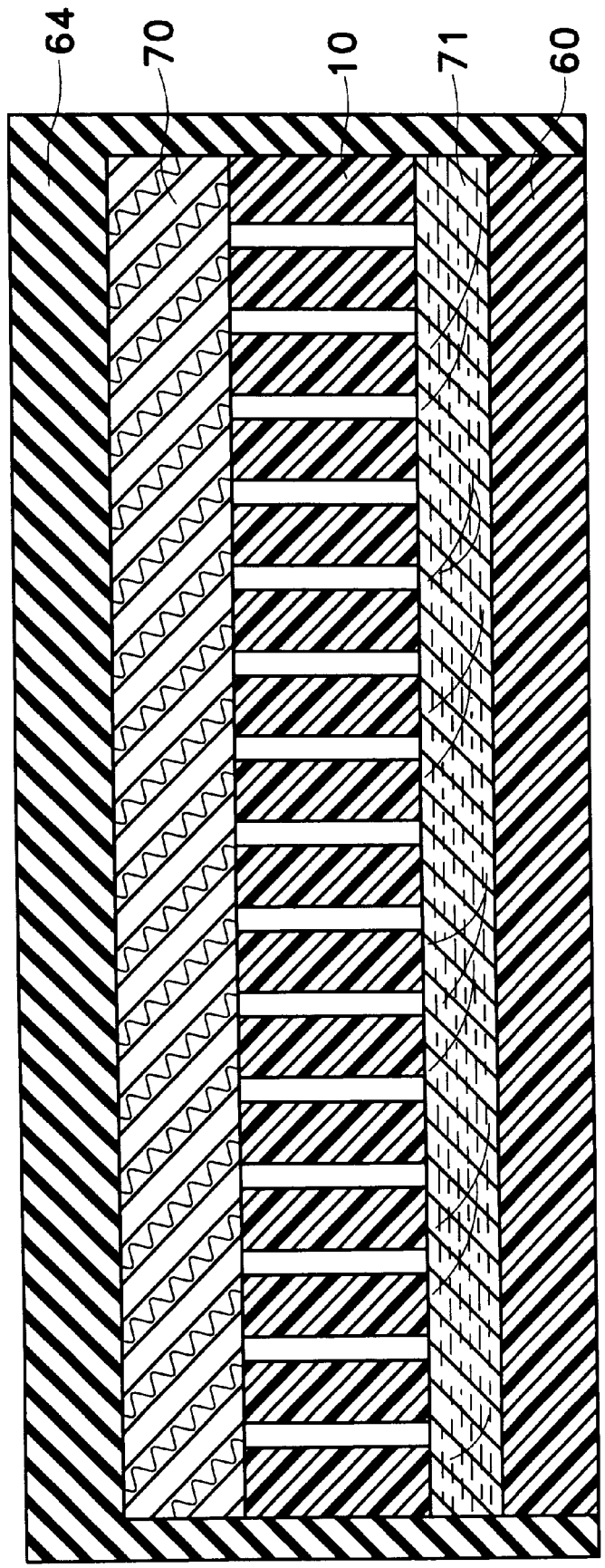
FIG. 9 is a cross-sectional view of a second alternative embodiment of the membrane-based formulation system of the present invention.

Moreover, the formulation system constructed in the form of the envelope 100 is only one embodiment of the present invention. Alternative constructions of a membrane-based formulation are also available. For example, as shown in FIG. 8, the filter 70 is positioned between the membrane 64 and the modulator 10. The substance passes through the channels offered by the holes 12 of the modulator 10, the filter 70 and the membrane 64 sequentially in order to reach the surrounding environment through the opening 62. Furthermore, as illustrated in FIG. 9, a membrane-based formulation system may be formed by placing chemical substance, a modulator 10 of the present invention and a membrane 64 over a backing 60 in geometric sequence and sealing the sides of the membrane 64 against the backing 60. Filter 70 is optionally. Also, a formulation system can be formed by a modulator of the present invention covering the substance against a backing, which provides support to the substance. This simple alternative embodiment may be useful when, say, a membrane is not handy.

The invention will be better understood by reference to the following illustrative examples, each example consisting of a performed experiment.

Materials and Methods
Preparation of type 1 formulations

The formulation device comprises several components assembled as shown in FIGS. 6(A)–(E). As an example, an envelope was prepared by heat sealing, using an impulse hot wire sealer, 6 mil (0.0254 millimeters) nonpermeable polyethylene backing containing a 1.17 cm diameter opening. The opening was covered with a semipermeable membrane consisting of either 1 mil high density polyethylene film (HDPE) manufactured by Consep Inc. of Bend, Oreg., or low density polyethylene (LDPE) of various thickness manufactured by Ain Plastics of Florida, Tampa, Fla. Lures of this type are typically formed in a 3.0×5.0 cm rectangle. A piece of 2.5×4.5 rectangular filter paper (Whatman #1), manufactured by Whatman Inc. of Haverhill, Mass., was placed in all formulations. In initial studies no modulator was used to provide a baseline for comparison. In subsequent formulations a modulator according to the present invention was added to the lure. The modulator consisted of a 1.5×4.0 cm$^2$ and 1.0 mm thick piece of perforated polypropylene containing about 36 holes/cm$^2$. Each hole was about 1 mm$^2$ in cross-section and this material was obtained from Darice Inc., Strongsville, Ohio. The chemicals under investigation were pipetted onto the filter paper and the top of the envelope was closed using a impulse hot wire sealer. In experiments where it was desired to decrease the exposed surface of the membrane a piece of aluminum tape manufactured by United Tape Company, Cumming, Ga. with a hole was placed over the existing membrane. This technique was use to prepare a variety of lures of different sizes vide infra.

Preparation of type 2 formulations

Lures were prepared similar to the type 1 formulation with the exception that the envelope consisted of low density polyethylene of various thicknesses manufactured by Ain Plastics of Florida, Tampa, Fla. Thus the lure was prepared from the material that also served as the membrane. Typically these lures were 3.0×9.0 cm$^2$ in size.

Experiment 1 (without modulator device)

Type 1 lures (3×5 cm) with a 5 mm diameter membrane (1 mil HDPE) were used. No modulator device was used in this experiment. Separate lures were loaded with 50 μl of either hexanol, ethyl hexanoate, cineole or ethyl octanoate as the test chemicals. Chemicals were purchased from Aldrich Chemical Company of Milwaukee, Wis. and were used without further purification. Purity of the chemicals was 98% based on gas chromatographic analyses.

Experiment 2 (with modulator device)

Lures were prepared as described in experiment 1, except that the modulator device was added to each lure.

Experiment 3, 4 and 5 (with modulator device)

Lures were prepared as described in experiment 2. In experiment 3 lures contained 50 μl of an equal mixture of hexanol, ethyl hexanoate, ethyl octanoate, and cineole. Experiment 4 was similar to experiment 3 and lures were loaded with variable amounts (5, 10, 25, 50 or 100 μl) of the four component blend. Experiment 5 measured release rates from lures containing 50 μl of a 10:10:1:1 (by volume) mixture of cineole, ethyl octanoate, hexanol and ethyl hexanoate respectively. A total of 50 μl of the blend was loaded into each lure.

Experiment 6 (with modulator device)

Type 1 lures (3×5 cm in size containing a 5 mm diameter membrane consisting of 6 mill LDPE) and a modulator device were loaded with either 5, 15, 25 and 50 μl of 2-methyl-6-vinyl pyrazine (2,6-MVP). The pyrazine was purchased from Fuji Flavour Co. LTD., Tokyo, Japan and the purity of this material was greater than 99% based on gas chromatographic analyses.

Experiment 7 and 8 (with modulator device)

Lures for experiment 7 consisted of type 1 lures with the modulator device having a size of 3.0×9.0 cm$^2$. The membrane used was 6 mill LDPE with a 1.17 cm diameter area of membrane exposed. Lures were loaded with 2 ml of TML. TML used was obtained from Albany International, Columbus, Ohio. Isomer content based on gas chromatographic analysis was determined to be 41.7% A, 5.1% 131, 14.7% B2, and 38.5% C. For comparison purposes the release rate of TML from commercially available plugs of TML, manufactured by Magnet lures, AgriSense®, Fresno, Calif., was also measured vide infra. For the purpose of this study we report only the release rate of isomer C, which has been shown to be the isomer that accounts for 98% of the attractiveness of TML, for example, in the 1990 Heath et al. paper mentioned above.

Release Rate Measurement Methodology

With the exception of one study, lures were maintained at room temperature during the course of the release rate determinations. When release rate measurement of the lures was not being done, lures were placed in a hood with an estimated air velocity of 0.25 m/sec. Generally, lures were placed in the hood for two days prior to initial analysis. In one study, lures were exposed in the field in McPhail type traps known in the art for a period of 30 day in Weslaco, Tex., and returned to Gainesville, Fla. for release rate measurements.

Release rates of emitted chemicals were determined using systems that have been previously described in the paper "Development and Evaluation of Systems to Collect Volatile Semiochemicals from Insects and Plants Using a Charcoal-Infused Medium for Air Purification" by Heath and Manukian, J. Chem. Ecol. 18(7), 1209–1226 (1992). The volatile collection system consists of a glass chamber (25.7 cm long and 7.6 cm ID) constructed of Pyrex glass with a glass frit inlet and a ground-glass joint outlet and a multiport collector base to which the collector traps were connected. Collector traps used to trap organic volatiles were made from a 4.0 cm long by 4.0 mm ID glass tube and contained 50 mg of Super-Q® as the adsorbent. Two stainless steel frits were used to contain the adsorbent. The collector traps were connected to stainless steel tubing using 0.64 cm unions and 0.64 cm ID Teflon® ferrules. These traps were cleaned by soxhlet extraction using methylene chloride for 24 hours and dried in a fume hood prior to initial use. Volatiles from the lures collected on the traps were eluted using two 50 μl rinses of high purity methylene chloride. Tetradecane was added as internal standard to the extracted material prior to analysis. Release rates were measured from a minimum of three lures per test day. Average release rates were used for linear regression analyses and determination of the formulation half-life.

Gas chromatographic analyses were conducted using a Hewlett-Packard Model 5890A Series 110 gas chromatograph, equipped with a cool on-column capillary injector (septum injector) and flame ionization detector. Helium was used as the carrier gas at a linear flow of 18 cm/sec. The chromatographic data was collected and processed using the Perkin-Elmer Nelson Turbochrom® III software running on an IBM-type 386 PC system under MS-Windows® 3.0. Capillary gas chromatography (CGC) analysis was done using a retention gap column prior to the capillary column. This system permitted the injection of samples without concentration in 5–100 pl of solvent. A combination of three fused silica columns connected in series using GlasSeala connectors manufactured by Supelco Inc., Bellefonte, Pa., was used. The primary deactivated fused silica column, 8.0 cm long by 0.5 mm ID, was connected between the injector and the retention gap column. This primary column permitted the use of 0.4 mm OD stainless steel needles with a septum injector for on-column injections. The retention gap column used was 10 m by 0.25 mm ID deactivated fused silica and the analytical column used for analysis was a 30 m by 0.25 mm ID (0.25 pm film) SE-30. The initial column temperature of 401° C. was maintained for 2 min. and the column was programmed to 200° C. at 10° C./min. Confirmation of compound identity was obtained using mass spectroscopy. Mass spectra were obtained using the capillary columns, operated as described above, coupled to a Finnigan Ion Trap® mass spectrometer in either electron impact (EI-ITDMS) or chemical ionization (CI-ITDMS) mode. The reagent gas used for CI was isobutane.

Results

Figure 10A:
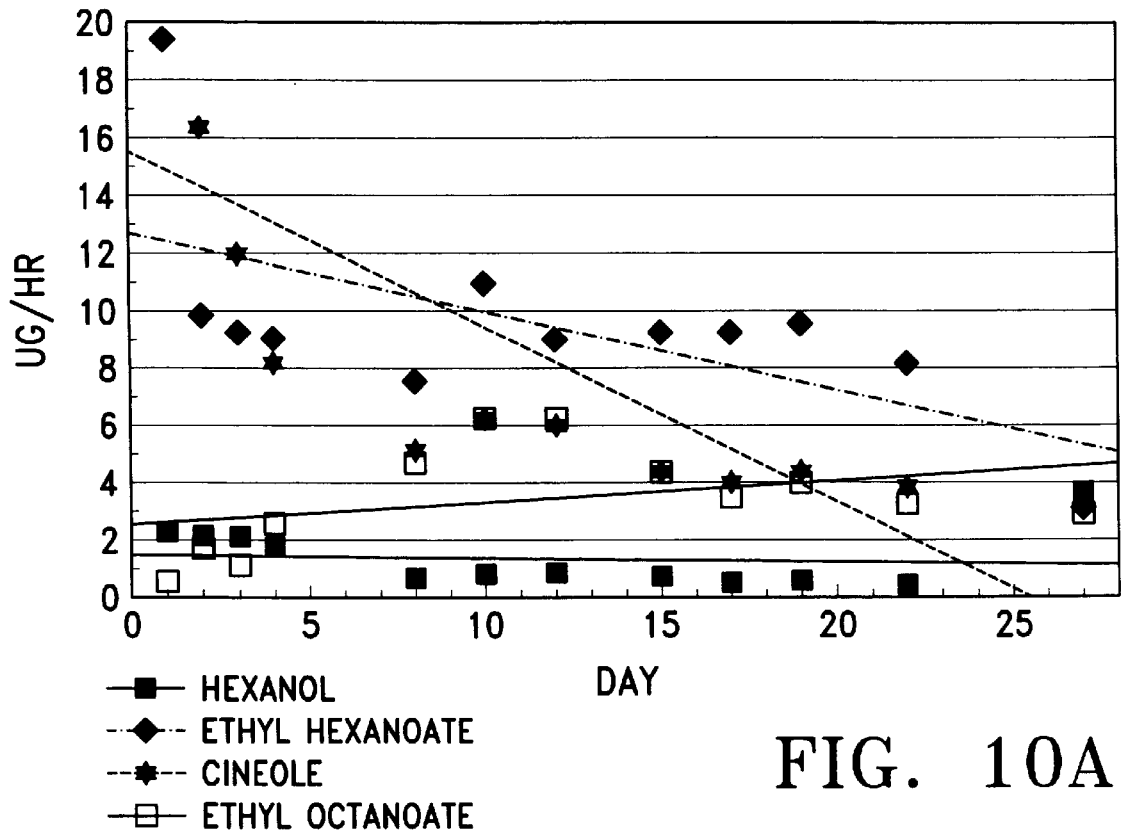
FIGS. 10(A)–(B) chart the observed release rates of lures loaded with 50 $\mu$l of either hexanol, ethyl hexanoate, ethyl octanoate, or cineole in the type 1 formulation: (A) no modulator of the present invention is used; (B) with the modulator according to one embodiment of the present invention.
Figure 10B:
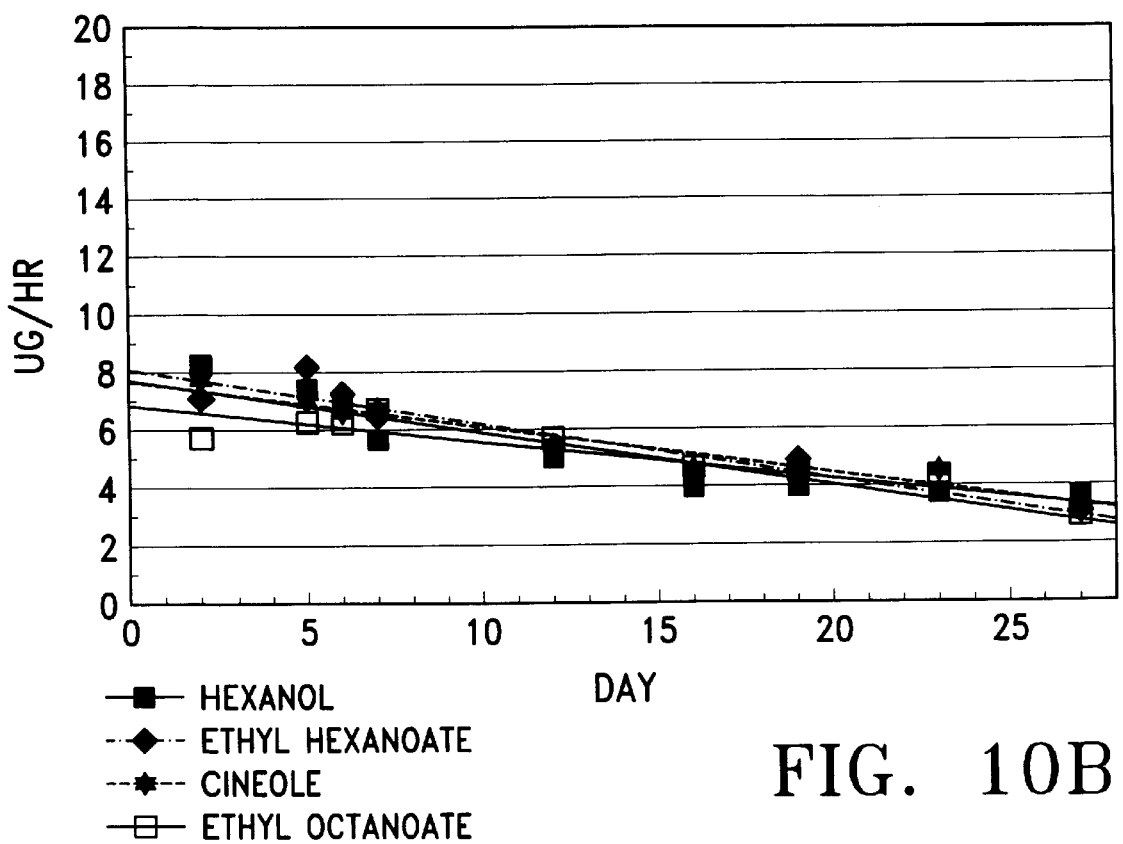

The results of experiment 1 are shown in FIG. 10(A) and in Table 1. These lures were loaded with 50 μl of either hexanol, ethyl hexanoate, ethyl octanoate, or cineole in the type 1 formulation and resulted in varying release rates. The half-lives of the lures were 22, 24 and 13 days for hexanol, ethyl hexanoate and cineole, respectively. The release of cineole followed a first-order type of release with a decrease in release rate after approximately three days as shown in FIG. 10(A). The release rate of ethyl octanoate increased during the first 10 days and subsequently decreased. In experiment 2, lures that were prepared similar to experiment 1 lures but with the addition of the modulator resulted in a decreasing linear release rate, as shown in FIG. 10(B), over the 27 days of testing. The half-life of hexanol, ethyl hexanoate, cineole, and ethyl octanoate were 21, 21, 24 and 27 days respectively, and the release rates over time were similar among the four chemicals (Table 2).

TABLE 1

REGRESSION ANALYSIS OF LURE PERFORMANCE (y = a + bx)
Experiment 1 - no release rate modulator

|  | a | b | $R^2$ | half-life in days |
|---|---|---|---|---|
| hexanol | 1.510 | −0.012 | 0.011 | 22 |
| ethyl hexanoate | 12.700 | −0.268 | 0.389 | 24 |
| cineole | 15.530 | −0.610 | 0.535 | 13 |
| ethyl octanoate | 2.510 | 0.081 | 0.140 | NA |

TABLE 2

REGRESSION ANALYSIS OF LURE PERFORMANCE (y = a + bx)
Experiment 2 - release rate modulator use

|  | a | b | $R^2$ | half-life in days |
|---|---|---|---|---|
| hexanol | 7.840 | −0.186 | 0.860 | 21 |
| ethyl hexanoate | 8.110 | −0.191 | 0.901 | 21 |
| cineole | 7.800 | −0.163 | 0.961 | 24 |
| ethyl octanoate | 6.910 | −0.130 | 0.861 | 27 |

TABLE 3

REGRESSION ANALYSIS OF LURE PERFORMANCE (y = a + bx)
Experiment 3 - release rate modulator - equal mixture

|  | a | b | $R^2$ | half-life in days |
|---|---|---|---|---|
| hexanol | 2.573 | −0.023 | 0.920 | 56 |
| ethyl hexanoate | 3.191 | −0.053 | 0.801 | 30 |
| cineole | 2.550 | −0.025 | 0.715 | 51 |
| ethyl octanoate | 2.611 | −0.040 | 0.886 | 33 |

TABLE 4

REGRESSION ANALYSIS OF LURE PERFORMANCE (y = a + bx)
Experiment 4 - release rate modulator - equal mixture at different lure load

|  | a | b | $R^2$ | half-life in days |
|---|---|---|---|---|
| hexanol | 0.120 | 0.036 | 0.991 |  |
| ethyl hexanoate | 0.219 | 0.037 | 0.968 |  |
| cineole | 0.202 | 0.035 | 0.991 |  |
| ethyl octanoate | 0.089 | 0.037 | 0.994 |  |

TABLE 5

REGRESSION ANALYSIS OF LURE PERFORMANCE (y = a + bx)
Experiment 5 - release rate modulator - a 1:1:10:10 mixture

|  | a | b | $R^2$ | half-life in days |
|---|---|---|---|---|
| hexanol | 0.605 | −0.003 | 0.923 | 101 |
| ethyl hexanoate | 0.565 | −0.002 | 0.924 | 141 |
| cineole | 5.590 | −0.027 | 0.972 | 104 |
| ethyl octanoate | 5.610 | −0.026 | 0.934 | 108 |

TABLE 6

REGRESSION ANALYSIS OF LURE PERFORMANCE (y = a + bx)
Experiment 6 -
release rate modulator - 2,6 methyl vinyl pyrazine a different loads

|  | a | b | $R^2$ | half-life in days |
|---|---|---|---|---|
| 5 μl | 0.133 | −0.001 | 0.584 | 67 |
| 15 μl | 0.367 | −0.001 | 0.586 | 184 |
| 25 μl | 0.599 | −0.001 | 0.496 | 300 |
| 50 μl | 1.250 | −0.013 | 0.683 | 48 |

TABLE 7

REGRESSION ANALYSIS OF LURE PERFORMANCE (y = a + bx)
Experiment 7 -
release rate modulator - Trimedlure (diameter of membrane = 1.17 cm)

|  | a | b | $R^2$ | half-life in days |
|---|---|---|---|---|
| 1 ml | 6.134 | −0.006 | 0.096 | 520 |

TABLE 8

REGRESSION ANALYSIS OF LURE PERFORMANCE (y = a + bx)
Experiment 8 - Trimedlure 2 ml

|  | a | b | $R^2$ | half-life in days |
| --- | --- | --- | --- | --- |
| Membrane system | 297.90 | −0.060 | 0.118 | Observed = 51 |
| Commercial lure | 229.38 | −4.652 | 0.941 | 25 |

Figure 11A:
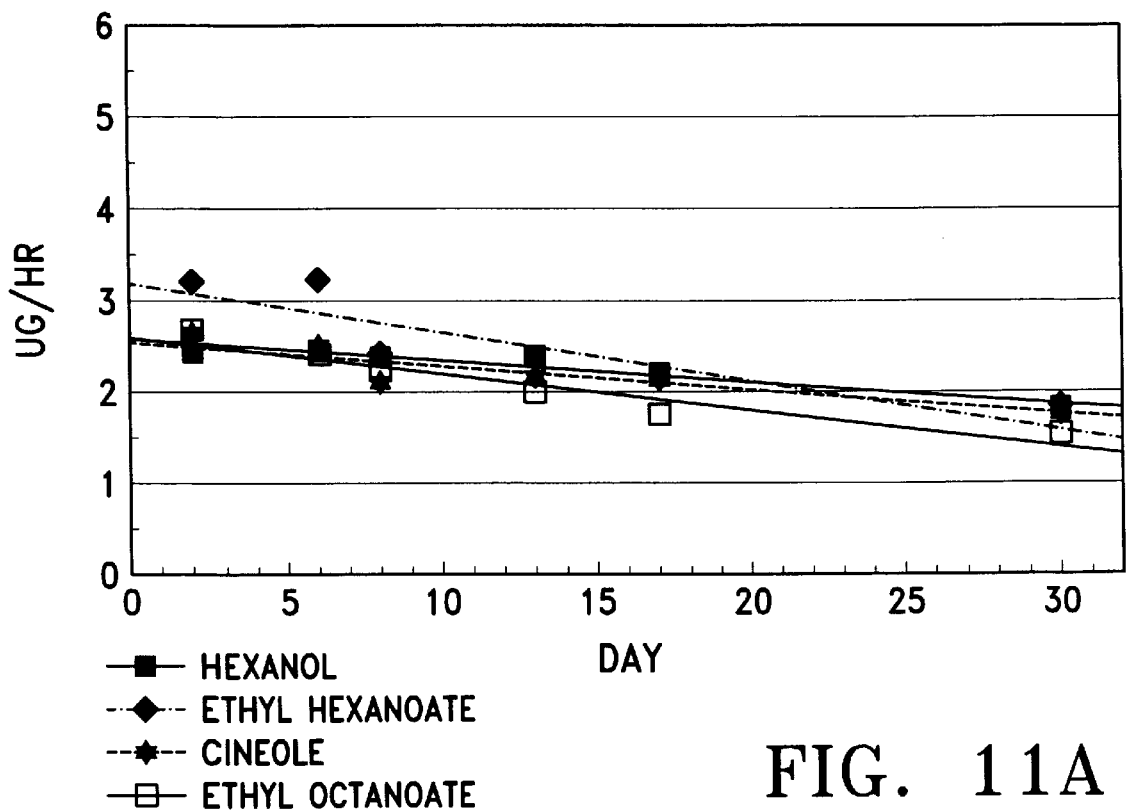
FIGS. 11(A)–(B) chart the observed release rates of lures with an equal mixture of hexanol, ethyl hexanoate, cineole and ethyl octanoate from type 1 formulation, with the modulator according to one embodiment of the present invention, with different loads: (A) with 50 $\mu$l load; and (B) with 5, 10, 25, 50 and 100 $\mu$l loads.
Figure 11B:
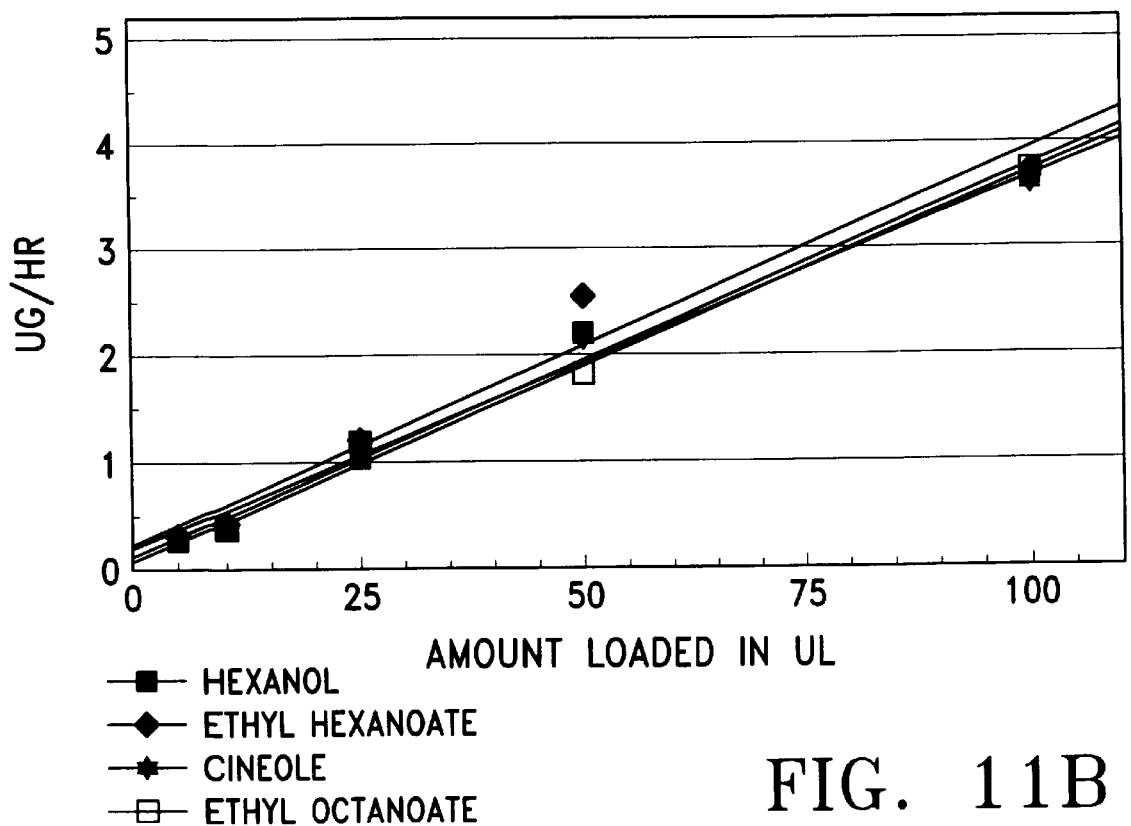

When the four chemicals were mixed in equal proportions in experiment 3 and the release rates determined over time the resultant release of the four chemicals was very similar as shown in FIG. 11(A). The half-lives of the four chemicals increased and ethyl hexanoate had the shortest half-life of 30 days (Table 3). The release rates of lures loaded in experiment 4 with 5, 10, 25, 50 and 100 μl of an equal mixture of the four compounds is shown in FIG. 11(B). Based on regression analyses (Table 4) there was a direct relationship between lure load and release rate. $R^2$ values for all the compounds when mixed in equal proportions were greater than 0.967.

Figure 12A:
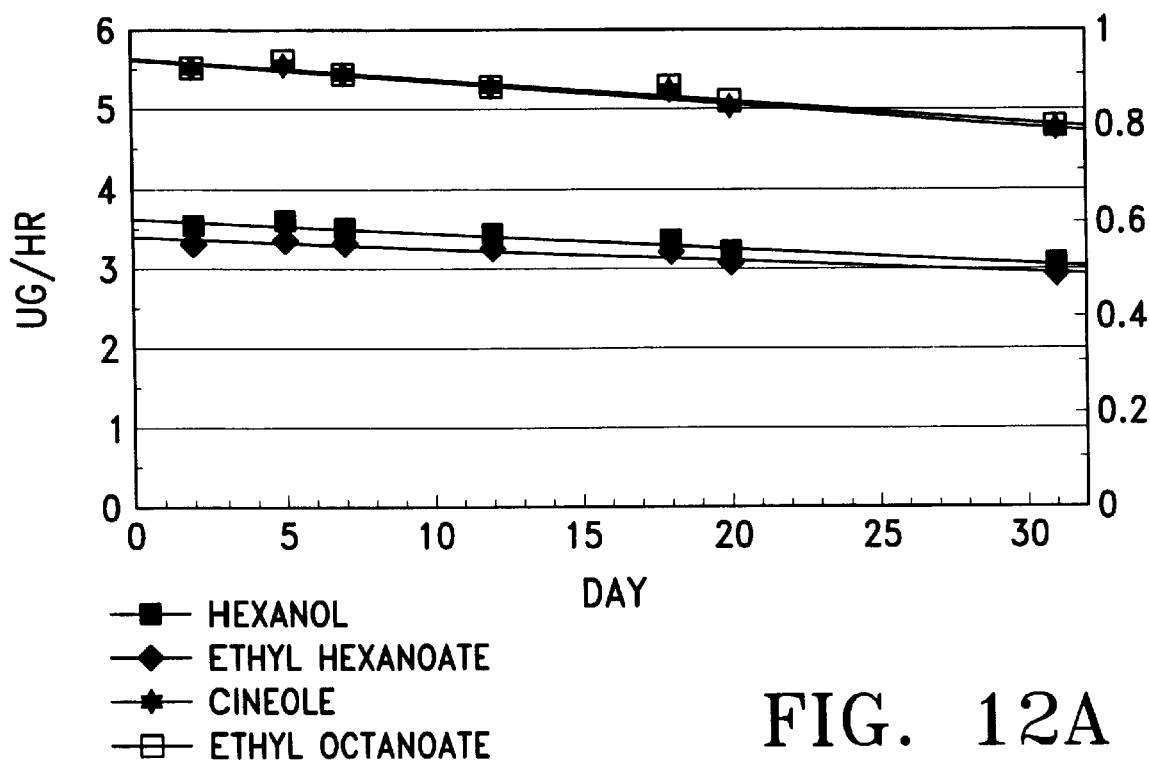
FIGS. 12(A)–(B) chart the observed results from type 1 formulation, with the modulator according to one embodiment of the present invention, when hexanol, ethyl hexanoate, cineole, and ethyl octanoate, were mixed in a 1:1:10:10 ratio, respectively: (A) release rates; and (B) percentage of compounds released over time from lures.
Figure 12B:
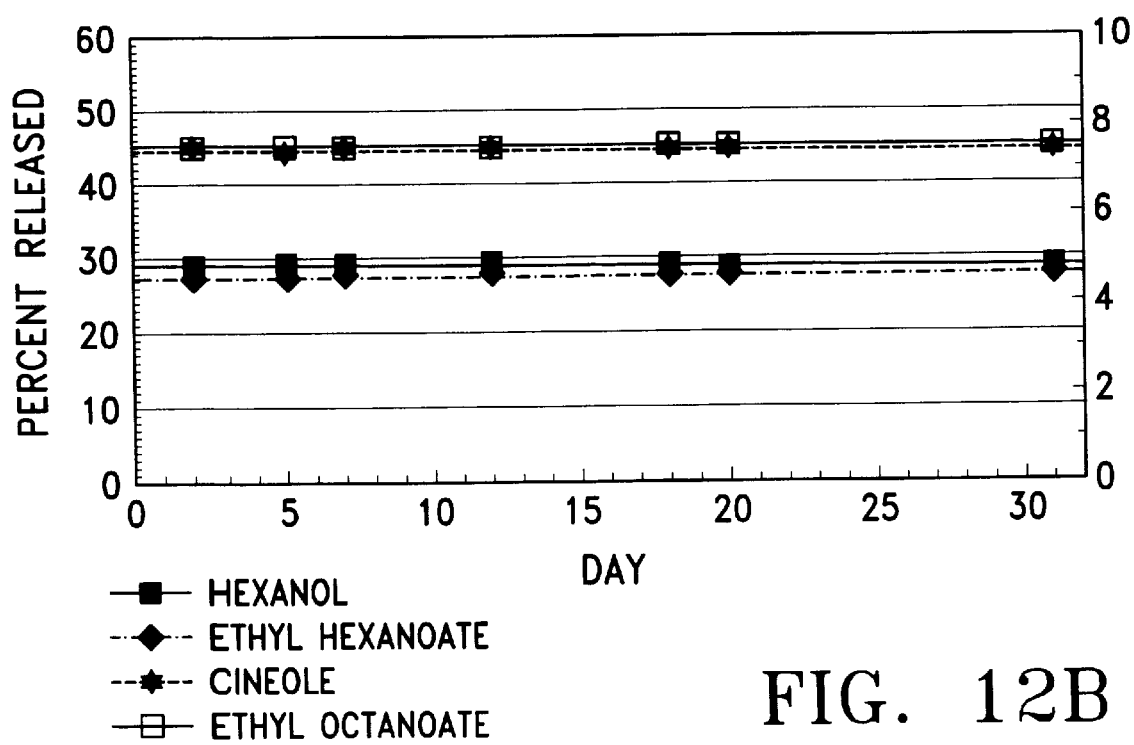

In experiment 5 we determined the release rate when cineole, ethyl octanoate, hexanol and ethyl hexanoate were mixed in a 10:10:1:1 ratio (by volume), respectively as shown in FIG. 12(A). The half-life of this lure was estimated to be approximately 101 days based on the compound having the shortest half-life, which was hexanol (Table 5). The other compounds had longer half-lives and ethyl hexanoate showed little decrease in release rate over the 31 days of testing. The percent of released compound is shown in FIG. 12(B). The expected percent of release of the compounds based on load ratio should be 45.5:45.5:4.5 and 4.5% for cineole, ethyl octanoate, hexanol and ethyl hexanoate, respectively. Percent release averaged standard development was 45.21+0.117, 45.39±0.134, 4.8+0.046, and 4.6±0.045 for cineole, ethyl octanoate, hexanol and ethyl hexanoate, respectively. The percentage of release of the four chemicals was constant during the 30 days that lures were analyzed as shown in FIG. 12(B). As part of this experiment lures that were exposed for approximately 30 days in Weslaco, Tex., at an approximate daytime temperature of 32° C. were analyzed. These lures released on an average 11, 3, 4 and 10 percent less cineole, ethyl octanoate, hexanol and ethyl hexanoate, respectively, than from lures held under laboratory conditions for a similar period of time. The average percent release after exposure in the field was 45.3±0.12, 46.6 0.145, 3.3±m45, and 4.8±0.044 for cineole, ethyl octanoate, hexanol and ethyl hexanoate, respectively.

Experiment 6 investigated the release rate of lures loaded with 5, 15, 25 and 50 μl of 2,6-MVP, referring to FIG. 13 and Table 6. All lures resulted in a zero-order release of this material. Based on measurements of release rate of lures loaded with 50 μl it was determined that emission of 2,6-MVP decreased by approximately 20% by day 17. Lures loaded with 5, 15 and 25 μl of 2,6-MVP resulted in an almost constant release rate over the 23 days that release rates were determined.

The results from experiment 7, which investigated the release of low amounts of TML over time, are shown in FIG. 14(A) and Table 7. These lures were of type 2, and 1 ml of TML was used. The average release rate of isomer C over the 250 days of analyses was 6.8±S.E. 0.5 and no decrease in emission rates were observed during this time. Experiment 8, which determined the release rate of type 2 lures using 6 mil LDPE and loaded with 2 ml of TML, indicated that a constant release of isomer C occurred for approximately 51 days as shown in FIG. 14 and Table 8. In comparison the release rate from the commercially prepared lure decreased over time and the half-life of these lures was determined to be 25 days as can be seen from FIG. 14 and Table 7.

Although the present invention has been described with reference to specific details of certain embodiments thereof, it is not intended that such details should be regarded as limitations upon the scope of the invention except as and to the extent that they are included in the accompanying claims. For example, instead of constructing an envelope by folding, it can be formed by sealing two pieces of backing together.

What is claimed is:

1. A device for releasing a volatile substance to a surrounding environment, comprising:
   a. a receptacle having an interior for containing the substance, wherein the receptacle is formed from a material essentially nonpermeable to the substance with at least one first opening to allow communication between the interior of the receptacle and the surrounding environment;
   b. a membrane selectively permeable to the volatile substance, wherein the membrane is contained within the receptacle;
   c. a release rate modulator positioned between the membrane and the substance, wherein the modulator comprises a perforated plate with a plurality of holes; and
   d. filter paper onto which the volatile substance is pipetted, wherein the filter paper is contained within the receptacle.

2. The device of claim 1, further comprising a tape covering with a second opening therethrough, wherein the tape covering is nonpermeable to the substance and is placed over the membrane with the second opening in communication with the first opening.

3. The device of claim 2, wherein the tape covering comprises a metal film.

4. The device of claim 3, wherein the metal film is an aluminum film.

5. The device of claim 2, wherein the second opening is smaller than the first opening.

6. The device of claim 1, wherein the receptacle comprises an envelope with two panels.

7. The device of claim 1, wherein the substance is a volatile material selected from the group consisting of insecticide compositions, herbicide compositions, perfume compositions, animal repellent compositions, air freshener compositions, pheromone compositions, odor maskant compositions, deodorant compositions, insect repellent compositions, compositions for the evaluation of olfactory functioning in humans as well as in animals and compositions for the treatment of disease of humans and animals through olfactory functioning.

8. The device of claim 1, wherein the membrane comprises a semipermeable membrane selected from the group consisting of high density polyethylene (HDPE) film and low density polyethylene (LDPE) film.

9. The device of claim 1, wherein the perforated plate comprises polypropylene.

10. The device of claim 1, wherein the perforated plate has a thickness between about 0.5 and 1.5 mm.

11. The device of claim 1, wherein the perforated plate is generally rectangular and the plurality of holes are distributed over the perforated plate in an array.

12. The device of claim 1, wherein the perforated plate is generally rectangular and the plurality of holes are distributed over the perforated plate diagonally.

13. The device of claim 1, wherein the perforated plate is generally circular and the plurality of holes are distributed over the perforated plate radially.

14. The device of claim 1, wherein the perforated plate is generally elliptic and the plurality of holes are distributed over the perforated plate radially.

15. The device of claim 1, wherein the plurality of holes are distributed over the perforated plate with a density between about 30 to 42 holes/cm$^2$.

16. The device of claim 1, wherein each of the plurality of holes is about 0.5 to 1.5 mm$^2$ in size cross-sectionally.

17. A device for transfer of a substance to a surrounding environment, comprising:
   a. a receptacle containing the substance on filter paper, wherein the receptacle has at least one opening; and
   b. a plate covering the substance on filter paper, wherein the plate has a plurality of holes providing channels for the substance to pass into the surrounding environment through the opening in a relatively consistent flow.

18. The device of claim 17 further comprising a membrane cooperating with the plate to modulate the passage of the substance, wherein the membrane is selectively permeable to the substance.

19. The device of claim 17, wherein the receptacle is formed from a material essentially nonpermeable to the substance.

20. The device of claim 17, wherein the plurality of holes are distributed over the plate with a density between about 30 to 42 holes/cm$^2$.

21. The device of claim 17, wherein each of the holes is about 0.5 to 1.5 mm$^2$ in size cross-sectionally.

22. The device of claim 17, wherein the plate has a thickness between about 0.5 and 1.5 mm.

23. A method for releasing a substance to a surrounding environment, comprising:
   a. providing a receptacle having an interior adapted to contain the substance and at least one first opening between the interior and the surrounding environment;
   b. loading the substance onto filter paper and placing the filter paper into the receptacle or installing filter paper into the receptacle and loading the substance onto the filter paper; and
   c. installing a perforated plate having a plurality of holes therethrough, the perforated plate substantially covering the substance, whereby release of the substance from the interior of the receptacle through the at least one first opening is modulated by the perforated plate.

24. The method of claim 23, further comprising a step of positioning a membrane next to the perforated plate, wherein the membrane is selectively permeable to the substance.

25. The method of claim 23, further comprising a step of placing a film with a second opening on top of the first opening, wherein the second opening communicates with the first opening.

26. The method of claim 23, wherein the plurality of holes are distributed over the perforated plate with a density in the range of about 30 to 42 holes/cm$^2$.

27. The method of claim 23 wherein each of the plurality of holes is about 0.5 to 1.5 mm$^2$ in size cross-sectionally.

28. The method of claim 23, wherein the perforated plate has a thickness in the range of about 0.5 to 1.5 mm.

* * * * *